United States Patent [19]

Carter

[11] Patent Number: 4,833,233

[45] Date of Patent: May 23, 1989

[54] HUMAN SERUM ALBUMIN CRYSTALS AND METHOD OF PREPARATION

[75] Inventor: Daniel C. Carter, Huntsville, Ala.

[73] Assignee: The United States of America as represented by the Administrator of the National Aeronautics and Space Administration, Washington, D.C.

[21] Appl. No.: 87,281

[22] Filed: Aug. 20, 1987

[51] Int. Cl.$^4$ .......................... C07K 3/24; C07K 3/28; C07K 15/00

[52] U.S. Cl. .................................. 530/363; 530/362; 530/364; 530/387; 530/422; 427/2; 428/408; 428/420; 428/478.2

[58] Field of Search ............... 530/362, 363, 364, 387, 530/422; 427/2; 428/408, 420, 478.2

[56] References Cited

U.S. PATENT DOCUMENTS

| | | | |
|---|---|---|---|
| 3,415,804 | 12/1968 | Polson | 530/387 X |
| 3,790,552 | 2/1974 | Johnson et al. | 530/387 X |
| 3,869,436 | 3/1975 | Falksveden | 530/364 |
| 4,164,496 | 8/1979 | Hao | 530/364 |
| 4,177,188 | 12/1979 | Hansen | 530/364 |
| 4,197,238 | 4/1980 | Murata et al. | 530/364 |
| 4,489,133 | 12/1984 | Kornberg | 530/422 X |
| 4,668,584 | 5/1987 | Uzgiris et al. | 530/422 X |

OTHER PUBLICATIONS

Vol. A of International Tables for Crystallography, Hahn, 1983, 422, No. 90.
J. Mol. Biol. (1974), 83, 551–555, McClure et al.
J. Biol. Chemistry, 251, No. 10, (1976), Rao et al.
Advances in Protein Chemistry, 37 (1985), pp. 180–181, Peters (Anfinsen et al. editors).

*Primary Examiner*—Howard E. Schain
*Attorney, Agent, or Firm*—William J. Sheehan; John R. Manning; Charles E. B. Glenn

[57] ABSTRACT

HSA crystals are provided in the form of tetragonal plates having the space groups P42$_1$2, the crystals being grown to sizes in excess of 0.5 mm in two dimensions and a thickness of 0.1 mm. Growth of the crystals is carried out by a hanging drop method wherein a precipitant solution containing PEG and a phosphate buffer is mixed with an HSA solution, and a droplet of mixed solution is suspended over a well of precipitant solution. Crystals grow to the desired size in 3 to 7 days. Concentration of reagents, pH and other parameters are controlled within prescribed limits. The resulting crystals exhibit a size and quality such as to allow performance of x-ray diffraction studies and enable the conduct of drug binding studies as well as genetic engineering studies.

18 Claims, 2 Drawing Sheets

HUMAN SERUM ALBUMIN CRYSTALS AND METHOD OF PREPARATION

ORIGIN OF THE INVENTION

The invention described herein was made by an employee of the United States Government and may be manufactured and used by or for the government of the United states of America for governmental purposes without the payment of any royalties thereon as therefor.

TECHNICAL FIELD

This invention relates to protein crystal growth and more particularly to the preparation of crystals of human serum albumin in a form and size suitable for x-ray studies of crystal structure.

BACKGROUND OF THE INVENTION

Serum albumin, a protein of multiple functions and manifold applications, is one of the most extensively studied proteins in biochemistry. Over 25,000 literature citations involving the biochemistry and/or applications of serum albumins have been published since 1969. The mammalian serum albumins proteins are known to be the product of three tandem gene duplications, and possess high helical content (60%) and high cystiene content (17 -disulphides) with approximate molecular weights in the range of 65,000 daltons. Complete amino acid sequences are known for bovine, rat, and human serum albumins. Although the principal function of serum albumin remains unknown, it contributes to many transport and regulatory processes. Many studies have focused on the multifunctional binding properties of this interesting protein which range from various metals, e.g. Ca and Cu, to fatty acids, hormones, and a wide spectrum of therapeutic drugs. The majority of these binding studies have involved the human serum albumin (HSA) and many have shown that the distribution, free concentration, and metabolism of various pharmaceuticals can be significantly altered as a function of the magnitude of binding to HSA.

A detailed knowledge of the three-dimensional structure of serum albumin is imperative in order to fully understand the binding modes as well as many of the physical properties of this multifaceted protein. In addition, since many newly developed pharmaceuticals are rendered less effective by HSA; it is apparent that the crystal structure of a serum albumin, particularly the human form, will find very broad and significant application in the area of rational drug design. Consequently, the serum albumins have been the subject of ongoing crystallographic investigation which includes the documentation of several crystal forms (Table 1). Because of difficulties with crystal size, quality, and/or reproducibility, the three-dimensional structure of a serum albumin remains unknown.

This invention is concerned with the methodology required to produce a new crystal form of HSA which can be grown reproducibly as large, relatively high quality crystals suitable for x-ray structure determination. Once the three dimensional structure has been determined it will become possible to learn the molecular details involved in the binding of the albumin with a large number of pharmaceutical compounds. This may be done by soaking crystals in an appropriate stabilizing solution which contains the drug molcules of interest. If the binding sites are available in this crystal form, a crystalline array containing the serum albumin protein and the drug molecule will be produced. Details of the molecular interaction between the drug and protein can then be determined by established procedures in x-ray crystallography.

Due to the multiple binding capabilities of HSA, knowledge of its three dimensional structure combined with suitable crystals, may also provide assistance in determining the structures of various small molecules and perhaps small proteins which have proven difficult to crystallize.

Crystals of human serum albumin have been known for some time. As early as 1952, large crystals of HSA had been grown. Detailed x-ray examination of these and other reported crystal forms, including crystals of Horse serum albumin were published by McClure and Craven in 1974 (1) See Table 1, below. Crystals of HSA have also been grown by Rao and co-workers (2). Table 1 summarizes the crystallographic data published to date on several human serum albumin crystal forms. According to Peters in a recent review (1985) on serum albumins (3):

Although readily crystallized, albumin has relinquished few of its secrets through x-ray crystallography to date.... Structural information from these crystals is awaited eagerly, but obtaining it appears to be fraught with obstacles. Low described monoclinic crystals as soft waxy, and crystals studied by Rao, et al. (1976) have tended to dissolve under study.

TABLE 1

| CRYSTAL DATA ON THE POLYMORPHS OF HUMAN SERUM ALBUMIN | | | | | |
|---|---|---|---|---|---|
| Crystal System | Monoclinic | Orthorhombic | Orthorhombic | Tetragonal | Tetragonal |
| Space Group | C2 | $P2_12_12_1$ | $P2_12_12$ | $P4_12_12$ or $P4_32_12$ | $P42_12$ |
| Unit Cell Dimensions | a = 126.5(3)<br>b = 39.2(1)<br>c = 135.2(3)<br>B = 93.3(1) | a = 155(1)<br>b = 83(1)<br>c = 122(1) | a = 137.3(1)<br>b = 275(3)<br>c = 58.02(2) | a = 84.0(5)<br>c = 276(3) | a = 187(1)<br>c = 81(1) |
| Unit Cell Volume $A^3$ | 668,900 | 1,570,000 | 2,125,000 | 1,947,000 | 2,832,000 |
| Molecules/ Asymmetric Unit | 1 | 2 | 3 | 1 | 2 |
| Diffraction Limits A | 2.7 | 3.7 | 3.0 | 3.8 | 2.9 |
| Matthews Coefficient* | 2.52 | 2.95 | 2.66 | 3.66 | 2.66 |
| Solvent Fraction | | 52% | 59% | 54% | 67% 54% |

TABLE 1-continued
CRYSTAL DATA ON THE POLYMORPHS OF HUMAN SERUM ALBUMIN

| Crystal System Monoclinic | | Orthorhombic | Orthorhombic | Tetragonal | Tetragonal |
|---|---|---|---|---|---|
| References | (1) | (1) | (2) | (1) | This work |

*Based on HSA MW 66458

References
1. R. J. McClure and B. M. Craven, J. Mol. Biol. (1974) 83, 551–555
2. Rao, S. N. et al. (1976) J. Biol. Chem., 251, 3191–3193
3. T. Peters, Advances in Protein Chemistry, Vol. 37, pg 161–243, (1985)

Crystals of the monoclinic form reported by McClure and Craven appear to be the highest quality; unfortunately, the crystals are small and difficult to reproduce. It is difficult to adequately compare the crystal quality of the remaining tetragonal crystal form with the tetragonal crystal form reported here, since the diffraction resolution reported for that crystal form was obtained with a conventional sealed tube source.

It is therefore an object of this invention to provide HSA in the form of crystals amenable to use in x-ray diffraction studies.

Another object is to provide HSA crystals having a size of at least 0.5 mm in two dimensions.

Yet another object is to provide HSA crystals in a form suitable for drug binding studies.

Still another object is to provide a method of preparing such crystals.

SUMMARY OF THE INVENTION

In accordance with the present invention human serum albumin crystals are provided in the form of tetragonal plates having the space groups P4$_2$1 2. These crystals may be readily grown to a size well in excess of 0.5 mm in two dimensions and a thickness of 0.1 mm, this size enabling effective x-ray diffraction studies from which molecular configuration may be deduced. The crystals grow from solutions of polyethylene glycol, which will provide for the added advantage of solubilizing various pharmaceutical and biological compounds for binding studies. Human serum albumin is known to undergo substantial conformational change with changes in pH. This crystal form is the only one to grow under conditions of physiological pH, and therefore will provide the most relevant information with regard to drug binding studies. Crystallization conditions are reproducible, and the crystals diffract to resolutions adequate to determine the nature of the binding modes of various biological and pharmaceutical compounds. Crystals prepared in accordance with the invention may also prove useful in conduct of genetic engineering studies.

Crystal growth may be readily carried out by a "hanging-drop" method using a polyethylene glycol solution and a monobasic potassium phosphate buffering agent, with solution pH being adjusted prior to initiation of crystal growth.

BRIEF DESCRIPTION OF THE DRAWINGS

Details of the invention will become apparent from the accompanying drawings wherein.

DETAILED DESCRIPTION OF THE INVENTION

Figure 1:
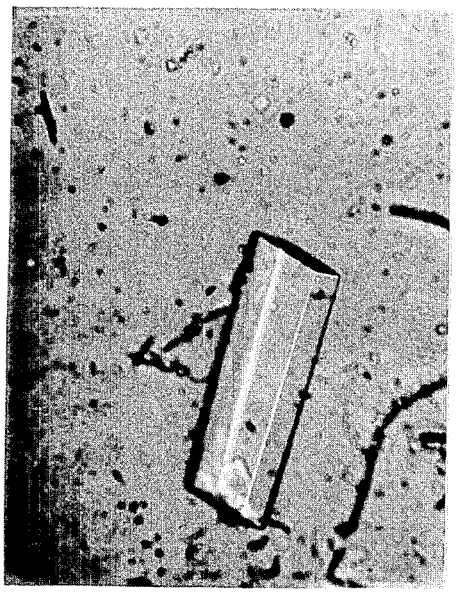
FIG. 1 is a photograph showing a crystal of HSA embodying the invention.

HSA crystals embodying the invention may be grown from a precipitant solution of polyethylene glycol (PEG), and a buffer, with concentration of reagents and pH being carefully controlled within prescribed limits. Any of the three basic techniques generally used for growth of protein crystals, that is, "hanging drop" or vapor diffusion, dialysis and batch methods may be employed, but the hanging-drop method is preferred.

In the hanging drop method a small drop of protein solution is placed on a cover slip, or glass plate, which is inverted over a well of solution and sealed. The solution in the well contains a precipitating agent, which is also present in a lesser amount in the protein droplet. The function of the precipitating agent is twofold. First, the solution in the well is initially at a lower vapor pressure than the protein droplet so that evaporation progresses at a rate fixed by the difference in the vapor pressures and the distance by which the vapor (usually water) must diffuse. Secondly, the precipitating agent lowers the solubility of the protein in solution by competing with the protein for available solvent, and thus as evaporation from the protein droplet occurs the solution becomes supersaturated in protein. Under the appropriate conditions including pH, protein concentration and temperature, crystallization of the protein or macromolecule then occurs.

The precipitant solution for use in the hanging drop method is made up to contain PEG at a molecular weight of 180 to 800, and preferably about 400 and a concentration of 35 to 45 volume percent, with best results being obtained at 40 volume percent, and a buffer in an amount sufficient to provide the required pH. Monobasic potassium phosphate at a concentration of 0.05 to 0.1M may be used for this purpose. Other buffers such as sodium acetate, sodium citrate and Tris (hydroxymethyl) aminomethane-maleate may also be used.

I have found that the pH of the precipitant solution obtained after mixing of PEG and buffer is critical to effective and reproducible growth of HSA crystals. A solution pH of 4.6 to 7.2 may be used, with best results being obtained at a pH of about 7.2. In a preferred procedure the precipitant solution pH is adjusted after mixing to compensate for variations in pH which may arise from variation in molecular weight and residue content of PEG. Adjustment of pH is readily carried out by addition of small amounts of a solution of a base such as potassium hydroxide or an acid such as hydrochloric acid until the desired value is obtained.

HSA may be provided in the form of an aqueous solution at a concentration of 90 to 200 mg per ml, with best results being obtained at 200 mg per ml. Use of HSA that is essentially free of fatty acids is preferred. In carrying out the hanging drop method a droplet of this solution, typically comprising 10 microliters, and a droplet containing an equal volume of precipitant solution would be placed on a cover slip and allowed to mix. A larger amount such as 1 ml of precipitant solution, without HSA, would be disposed in the well of the apparatus.

Crystals grow from these periods in 3 to 10 days to dimensions of $0.05 \times 0.5 \times 0.5$ mm to $2.0 \times 2.0 \times 0.3$ mm. The variations in the times for crystal growth are a function of protein concentration and pH. At concentrations of 200 mg per ml and pH values from 6.8 to 7.2 growth times are typically 5 days. For x-ray diffraction experiments the crystals are transferred from the hanging drop to a 10 to 20 microliter droplet of the corresponding reservoir solution, i.e. 40% PEG 400 in 0.05 M phosphate buffer. The crystals are stable in these solution at 4 C for long periods of time. The pH of this stabilizing solution may be adjusted to enhance the binding of molecules for diffraction studies, in most cases without destroying the crystals.

The dialysis method utilizes a semipermeable size exclusion membrane which retains the protein but allows smaller molecules (buffers and precipitating agents) to diffuse in and out. Essentially identical conditions to those determined for the hanging drop method (or vice versa) can then be used to grow protein crystals. In dialysis, rather than concentrating the protein and the precipitating agent by evaporation, the precipitating agent is allowed to slowly diffuse through the membrane and reduce the solubility of the protein keeping the protein concentration fixed.

The batch methods generally involve the slow addition of a precipitating agent to an aqueous solution of protein until the solution just becomes turbid, at this point the container is sealed and left undisturbed for a predetermined time.

In practice, once the appropriate precipitating agent(s) buffer(s) and other experimental variables have been determined for any given growth method, any of these methods or others unmentioned could be used to grow crystals of a given protein. Thus these features as described above for growing HSA by the hanging drop method may also be applied to growing HSA by batch or dialysis methods.

The invention is further illustrated by the following specific examples.

EXAMPLE 1

Crystals of HSA were grown from PEG using hanging drop procedures and apparatus. 5 $\mu$l portions of 35 to 40 percent PEG (molecular weight 400) in 0.05M $KH_2PO_4$, pH 4.6, were added to equal portions of 120 to 180 mg/ml HSA, placed on glass cover slips inverted and sealed over wells containing 1 ml 40 percent PEG in 0.1 M $KH_2PO_4$. Crystals appeared in 24 to 48 hours in the form of tetragonal plates and reached a size of 0.6 by 0.3 mm by 0.1 mm thick in 3 to 4 days. A photograph of one of the resulting crystals is shown in FIG. 1 of the drawings.

Figure 2:
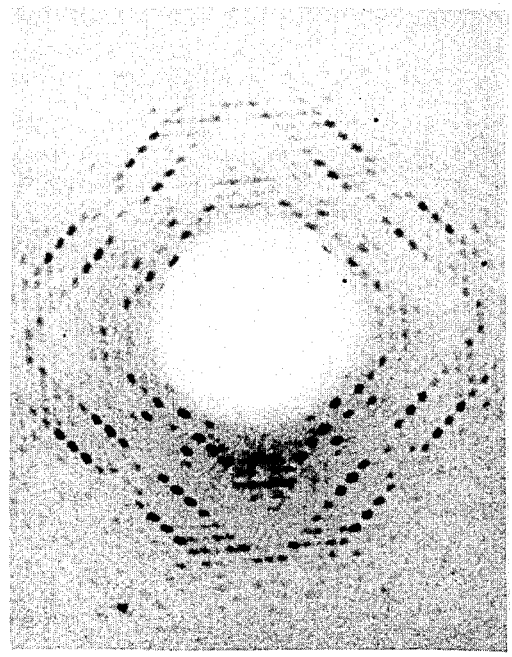
FIG. 2 is an x-ray precession photograph of such a crystal.

Crystals prepared as described above were transferred to a stabilizing solution of 35 to 40 percent PEG 400 in 0.1 M $KH_2PO_4$ and mounted in glass capillaries. X-ray precession photographs of resulting crystals were taken on a Supper camera with a Rigaku RU200 rotating anode source. An x-ray precession photograph thus obtained is shown in FIG. 2 of the drawings.

EXAMPLE 2

Figure 3:
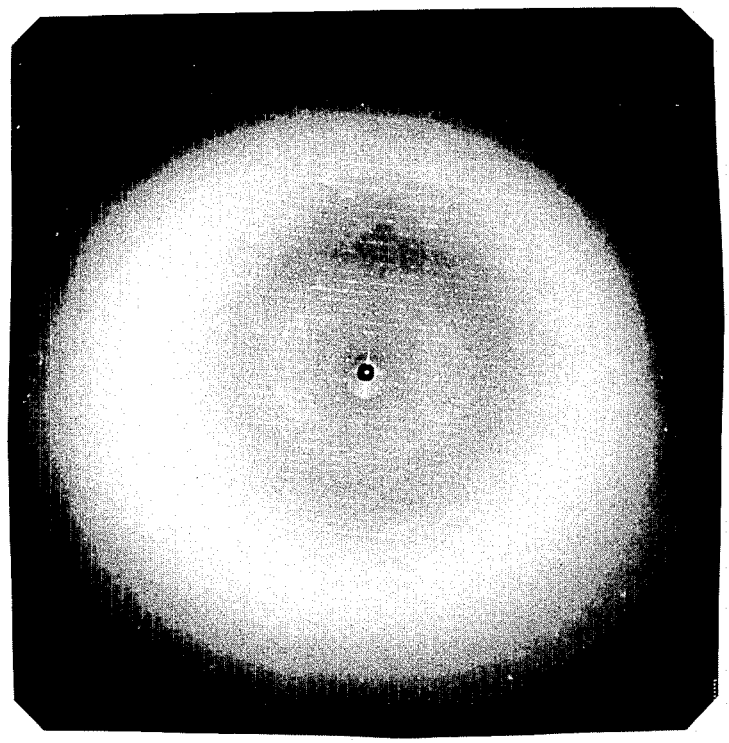
FIG. 3 is an x-ray oscillation photograph of an HSA crystal.

HSA crystals were grown by the procedure of Example 1, except that the concentration of $KH_2PO_4$ was 0.1M in the precipitant solution, and solution pH was adjusted to 6.2 prior to mixing with HSA. Oscillation photographs were taken on an Enraf-Nonius Arndt-Wanacott camera at the Brookhaven Synchrotron Light Source operating at 2.5 GeV with a beam current between 120 and 45 ma. An oscillation photograph so obtained is shown in FIG. 3 of the drawings.

X-ray procession photographs indicate 4 mm symmetry for the hko zone and mm symmetry for the hh1, h01 and 0k1 zones. The h00 and 0k0 zones show systematic absences for h or $k = 2n+1$. There are no systematic absences along the 001 direction. The space group is therefore concluded to be $P4_21 2$. Consistent with the presence of an isotropic axis, the crystals do not extinguish polarized light when viewed down the four fold axis. Unit cell constants as measured from precession photographs were found to be $a = b = 187(1)$ and $c = 81(1)$ A. A crystal density of 1.138 g/cm$^3$ was determined using aqueous Ficoll gradients. This value for density indicates two protomers per asymmetric unit, which corresponds to a Matthews coefficient of 2.6 Å$^3$/dalton and implies a solvent content of 54 percent.

Figure 4:
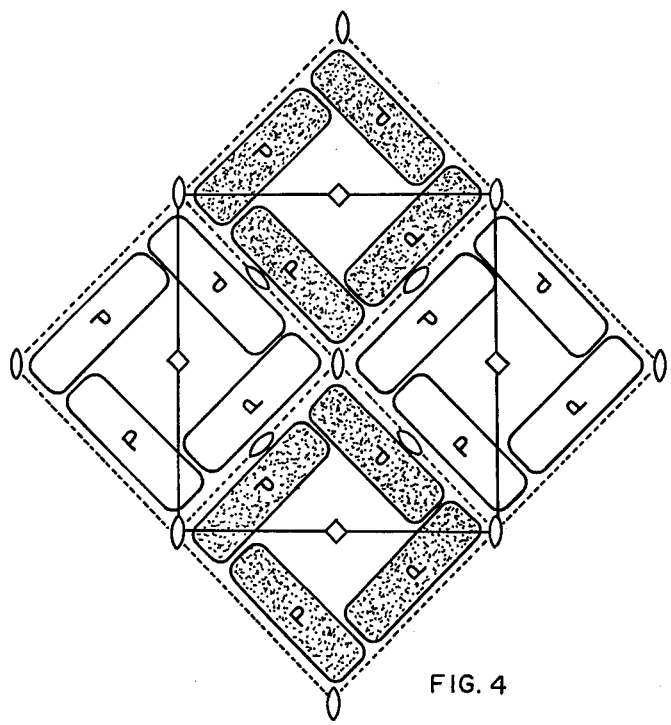
FIG. 4 is a schematic drawing showing a proposed packing arrangement of HSA molecules in crystals prepared in accordance with the invention.

FIG. 4 of the drawing illustrates a proposed orientation of the two molecules in the asymmetric unit of the $P4_21 2$ form. In this packing arrangement the shaded and unshaded molecules are related by a pseudo two-fold rotation forming a subcell with axes $a' = b' = 132$ Å as required and possessing a molecular length of 100 Å. Packing considerations in this case appear to limit the molecular length to values of 130 Å or less and values near 100 to 110 Å seem more appropriate, although solution and electron diffraction studies estimate a molecular length of 140 Å. The subcell shown in FIG. 4 would possess P422 pseudo-symmetry and contain one molecule per asymmetric unit.

While a preferred embodiment of the invention has been described using specific terms, such description is for illustrative purposes only, and it is to be understood that changes and variations may be made without departing from the spirit or scope of the following claims.

I claim:

1. An HSA crystal in the form of tetragonal plates having the space group $P4_21 2$ and the following unit cell constants: $a = b = 187(1)$A, $c = 81(1)$.

2. A crystal as defined in claim 1 having a size of at least 0.5 mm in two dimensions and a thickness of at least 0.05 mm.

3. A crystal as defined in claim 2 having a size of $0.5 \times 0.5 \times 0.05$ mm to $2.0 \times 2.0 \times 0.3$ mm.

4. A crystal as defined in claim 1 having a crystal density of 1.138 g/cm$^3$.

5. The method of growing crystals of HSA which comprises:
   providing an aqueous solution of HSA at a concentration of 90 to 200 mg per ml;
   providing an aqueous precipitant solution comprising PEG at a concentration of 35 to 45 volume percent and a buffer at a concentration such as to povide a pH of 4.6 to 7.2;
   mixing a droplet of said HSA solution with a droplet of said precipitant solution;

suspending the resulting mixed droplet over a well of precipitant solution in a sealed container, the vapor pressure of the solution in said well being lower than in the resulting solution in the mixed droplet; and allowing the suspended mixed droplet to stand for a prolonged period until an HSA crystal therein grows to a predetermined size.

6. The method of claim 5 wherein said buffer is monobasic potassium phosphate.

7. The method of claim 6 wherein the concentration of said buffer is 0.05 to 0.1 M.

8. The method of claim 7 wherein said precipitant solution is prepared by mixing a PEG solution with a buffer and adjusting the pH of the resulting mixed solution.

9. The method of claim 8 wherein said mixed droplet is allowed to stand for a period of 3 to 7 days.

10. The method of claim 9 wherein said mixed droplet is allowed to stand until said crystal grows to a size of $0.5 \times 0.5 \times 0.05$ mm to $2.0 \times 2.0 \times 0.3$ mm.

11. The method of claim 10 wherein the molecular weight of said PEG is 180 to 800.

12. The method of claim 11 wherein the average molecular weight of said PEG is about 400.

13. The method of claim 12 wherein the concentration of HSA in said aqueous solution is about 200 mg per ml.

14. The method of claim 7 wherein the pH of said precipitant solution is adjusted to a value of 6.8 to 7.2.

15. The method of claim 14 wherein said pH is adjusted to a value of 7.2.

16. The method of growing crystals of HSA which comprises:

providing an aqueous solution of HSA at a concentration of 90 to 200 mg per ml;

providing an aqueous precipitant solution comprising PEG at a concentration of 35 to 40 volume percent and a buffer at a concentration such as to provide a pH of 4.6 to 7.2;

combining said HSA solution with said precipitant solution and allowing the resulting solution to stand for a predetermined period until an HSA crystal therein grows to a predetermined size.

17. The method of claim 16 wherein said HSA solution is disposed within a semipermeable size exclusion membrane and said precipitant solution is combined with the HSA solution by diffusion through said membrane.

18. The method of claim 16 wherein said precipitant solution is combined with said HSA solution by slow addition thereto and the resulting solution is left to stand in a sealed container.

* * * * *